(12) United States Patent
Zheng et al.

(10) Patent No.: US 12,416,572 B2
(45) Date of Patent: Sep. 16, 2025

(54) METHOD FOR RAPID PREDICTION OF POTENTIAL OF PORPHYRY COPPER MINERALIZATION BASED ON SPECTRAL CHARACTERISTICS OF TOURMALINE

(71) Applicants: CHINA UNIVERSITY OF GEOSCIENCES (BEIJING), Beijing (CN); Tibet Julong Copper Co., Ltd., Lhasa (CN)

(72) Inventors: Youye Zheng, Beijing (CN); Hongjun Cheng, Beijing (CN); Jiancuo Luosang, Lhasa (CN); Jiangang Wei, Lhasa (CN); Xiaofang Dou, Beijing (CN); Qiong Ci, Lhasa (CN); Xiaofeng Liu, Lhasa (CN); Zhuoga Suolang, Lhasa (CN); Song Wu, Lhasa (CN)

(73) Assignees: CHINA UNIVERSITY OF GEOSCIENCES (BEIJING), Beijing (CN); Tibet Julong Copper Co., Ltd., Lhasa (CN)

( * ) Notice: Subject to any disclaimer, the term of this patent is extended or adjusted under 35 U.S.C. 154(b) by 197 days.

(21) Appl. No.: 18/492,788

(22) Filed: Oct. 24, 2023

(65) Prior Publication Data

US 2025/0012716 A1    Jan. 9, 2025

(30) Foreign Application Priority Data

Jul. 7, 2023 (CN) .......................... 202310870712.8

(51) Int. Cl.
*G01N 21/35* (2014.01)
*G01N 1/34* (2006.01)
(Continued)

(52) U.S. Cl.
CPC ........... *G01N 21/3563* (2013.01); *G01N 1/34* (2013.01); *G01N 33/24* (2013.01)

(58) Field of Classification Search
CPC ....... G01N 21/3563; G01N 1/34; G01N 33/24
See application file for complete search history.

(56) References Cited

U.S. PATENT DOCUMENTS

| 10,281,434 B2 | 5/2019 | Lippert-gellissen et al. |
| 11,378,563 B2 | 7/2022 | Abedini |
| 11,726,060 B2 | 8/2023 | Calvo et al. |

OTHER PUBLICATIONS

Ehrenfeld et al. (HIDSAG: Hyperspectral Image Database for Supervised Analysis in Geometallurgy, Scientific Data, 2023 10:164, https://doi.org/10.1038/s41597-023-02061-x, www.nature.com/scientificdata) (Year: 2023).*

* cited by examiner

*Primary Examiner* — Hugh Maupin
(74) *Attorney, Agent, or Firm* — True Shepherd LLC; Andrew C. Cheng

(57) ABSTRACT

A method for rapid prediction of porphyry copper mineralization potential based on spectral characteristics of tourmaline, includes collecting and collating data related to magma-fluid evolution, petrography and mineralogy of a porphyry copper deposit in a working area, systematically, distinguishing magmatic tourmaline from hydrothermal tourmaline in the working area, and further distinguishing phases and generations of the hydrothermal tourmaline; collecting hydrothermal tourmaline samples of the same phase and generation; performing short-wave infrared spectroscopy measurement on the collected hydrothermal tourmaline samples; extracting spectral characteristics of the Fe—OH wavelength and Mg—OH wavelength of the tourmaline samples based on The Spectral Geologist (TSG); and when the Fe—OH wavelength is less than 2245.75 nm, and the Mg—OH wavelength is greater than 2356.57 nm in the short-wave infrared spectrum of the samples, indicating that (Continued)

the porphyry copper deposit in an area where the samples are located has a great metallogenic potential.

7 Claims, 4 Drawing Sheets

(51) Int. Cl.
*G01N 21/3563* (2014.01)
*G01N 33/24* (2006.01)

METHOD FOR RAPID PREDICTION OF POTENTIAL OF PORPHYRY COPPER MINERALIZATION BASED ON SPECTRAL CHARACTERISTICS OF TOURMALINE

CROSS-REFERENCE TO RELATED APPLICATIONS

This application claims priority to Chinese Patent Application No. 202310870712.8 with a filing date of Jul. 7, 2023. The content of the aforementioned application, including any intervening amendments thereto, is incorporated herein by reference.

TECHNICAL FIELD

The present invention belongs to the technical field of mineral exploration, and in particular relates to a method for rapidly predicting the potential of porphyry copper mineralization.

BACKGROUND

Porphyry deposits are a main source of copper, molybdenum, gold, and rare metals worldwide, and have attracted widespread attentions from global geological explorers due to the characteristics of large scale, shallow burial, low grade, and easy mining. The traditional geochemical exploration method plays an important role in delineating a target zone of porphyry copper deposits in the early stage of porphyry copper deposit exploration. However, due to the development of hydrothermal alteration zones from several square kilometers to tens of square kilometers on the surfaces of the porphyry deposits, the traditional geochemical exploration method is obviously insufficient in further determining hydrothermal and mineralization centers, while trenching and drilling engineering reveal that the cost is high, the efficiency is low, the period is long, and the ecological environment is greatly damaged, which cannot meet the needs of mining enterprises to determine mineralization/hydrothermal centers in a short period of time.

In recent years, significant progress has been made in guiding mineral exploration and prospecting by utilizing the short-wave infrared spectral characteristics of altered minerals (such as muscovite, chlorite, alunite, and epidote) to delineate mineralization/hydrothermal centers. However, the altered minerals such as muscovite and chlorite in the porphyry deposits only occur in specific alteration stages and spatial ranges, are greatly affected by the composition of wall rocks and fluids, and often show irregular or opposite trends in guiding mineral exploration, which greatly puzzles the further evaluation of the potential of porphyry copper mineralization.

SUMMARY OF PRESENT INVENTION

In view of the problems that exploration law of altered minerals is unclear, and the potential of porphyry copper mineralization cannot be predicted rapidly, the present invention provides a method for rapid prediction of the potential of porphyry copper mineralization based on spectral characteristics of tourmaline. The short-wave infrared spectral characteristics of tourmaline have a single regularity, and can accurately predict and evaluate the potential of the porphyry copper mineralization, and eliminate the interference of multiplicity, and tourmaline has stable physical and chemical properties, with a distribution range throughout the entire hydrothermal evolution process.

To achieve the above objective, the technical solutions adopted are as follows:

a method for rapid prediction of the potential of porphyry copper mineralization based on spectral characteristics of tourmaline, including the following steps of:

(1) collecting and collating data related to magma-fluid evolution, petrography and mineralogy of a porphyry copper deposit in a working area, systematically, distinguishing magmatic tourmaline from hydrothermal tourmaline in the working area, and further distinguishing phases and generations of the hydrothermal tourmaline;

(2) collecting hydrothermal tourmaline samples of the same phase and generation;

(3) performing short-wave infrared spectroscopy measurement on the collected hydrothermal tourmaline samples;

(4) extracting spectral characteristics of the Fe—OH wavelength and Mg—OH wavelength of the tourmaline samples based on The Spectral Geologist (TSG); and (5) if the Fe—OH wavelength is less than 2245.75 nm, and the Mg—OH wavelength is greater than 2356.57 nm in the short-wave infrared spectrum of the samples, indicating that the porphyry copper deposit in an area where the samples are located has a great metallogenic potential; and if the Fe—OH wavelength is greater than 2245.75 nm, and the Mg—OH wavelength is less than 2356.57 nm in the short-wave infrared spectrum of the samples, indicating that the porphyry copper deposit in an area where the samples are located has a small metallogenic potential.

According to the above solution, in the step 1, a cause of formation of tourmaline is divided into magmatic tourmaline or hydrothermal tourmaline according to a process of magma-fluid evolution of the porphyry copper deposit.

According to the above solution, in the step 1, the phases and generations of the hydrothermal tourmaline closely related to mineralization are determined by combining petrographic and mineralogical characteristics with cut-through relationship and matrix support information.

According to the above solution, a collection area in the step 2 includes the surface, and interior and periphery of an ore body in drill holes.

According to the above solution, structural types of the collected tourmaline samples in the step 2 include a disseminated type, a finely veined type, and a dotted type.

According to the above solution, the step 3 further includes washing and drying the collected tourmaline samples to avoid the influence of impurities on the spectral characteristics.

Compared with the prior art, the beneficial effects of the present invention are as follows:

in terms of the selection of altered minerals in porphyry deposits, conventional exploration indicators for altered minerals such as muscovite and chlorite appear in specific stages, and are distributed in specific spaces, which have limitations on representing the entire mineralization process, and tourmaline has stable physical and chemical properties, with distribution ranges throughout the entire hydrothermal evolution process.

In terms of utilizing the short-wave infrared spectroscopy technology to guide prospecting and exploration of porphyry deposits, conventional exploration indicators for altered minerals such as muscovite and chlorite in different regions show opposite or irregular trends in the regularity of short-wave infrared spectral characteristics indicating mineralization centers, while the short-wave infrared spectral characteristics of tourmaline have a single regularity, and can accurately predict and evaluate the potential of porphyry copper mineralization, and eliminate the interference of multiplicity.

In the present invention, the potential of porphyry copper mineralization is rapidly predicted based on the spectral characteristics of the tourmaline, which solves the problems of long sample collection and preparation period, high cost, and low efficiency of analysis using electronic probes (EPMA) or an inductively coupled plasma mass spectrometer (LA-ICPMS). At the same time, the short-wave infrared spectral characteristics of the tourmalines such as Fe—OH (2250 nm) and Mg—OH (2350 nm) have good linear relationships with mineralization centers, and copper grades. Its advantage is that exploration indicators for tourmaline altered minerals are reliable, low in cost, and highly efficient, and can quickly characterize the potential of the porphyry copper mineralization.

DETAILED DESCRIPTION OF THE EMBODIMENTS

The following embodiments further illustrate the technical solutions of the present invention, but are not intended to limit the scope of protection of the present invention.

Figure 1:
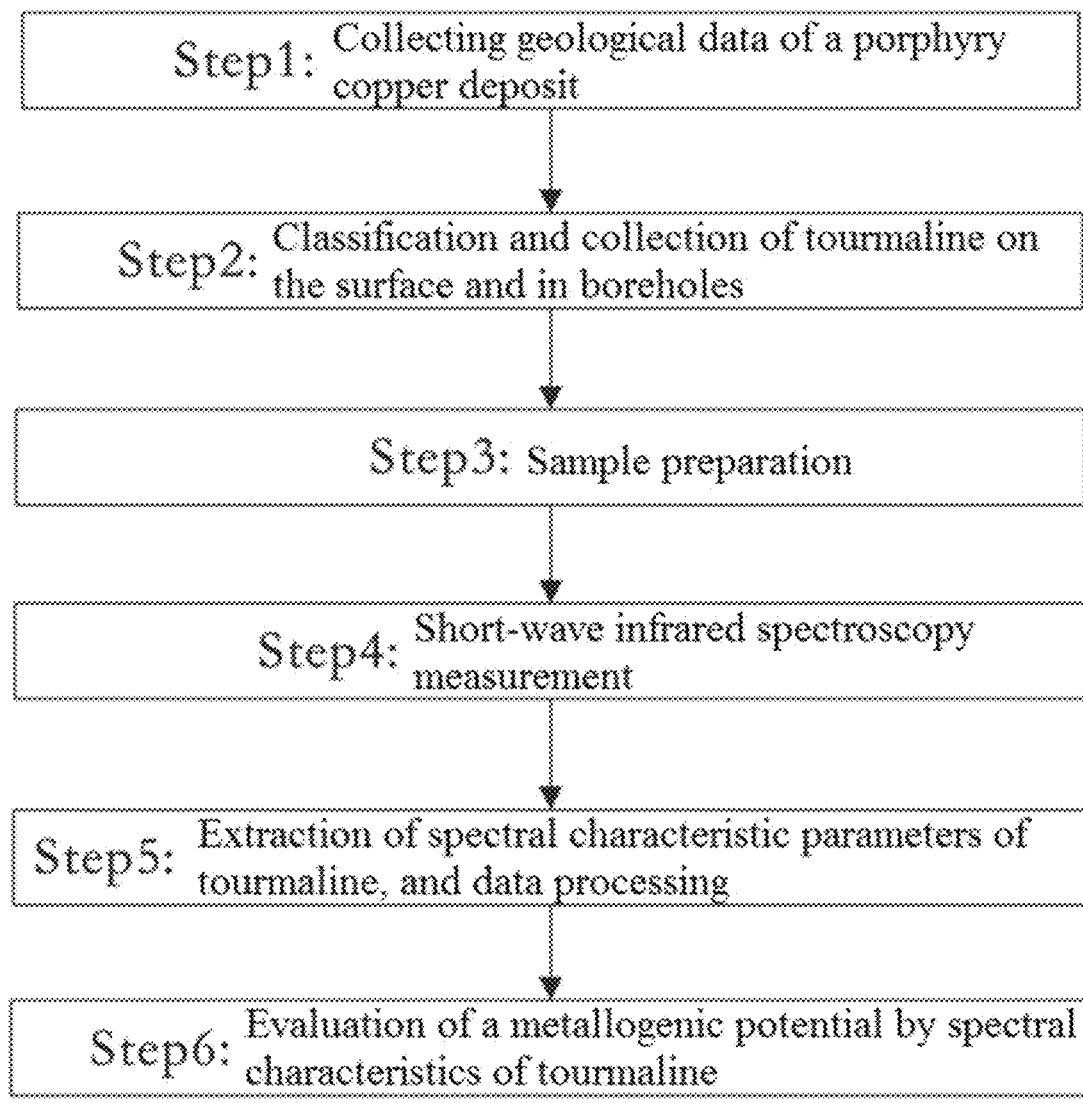
FIG. 1: a flow diagram of a method of the present invention.
Figure 2:
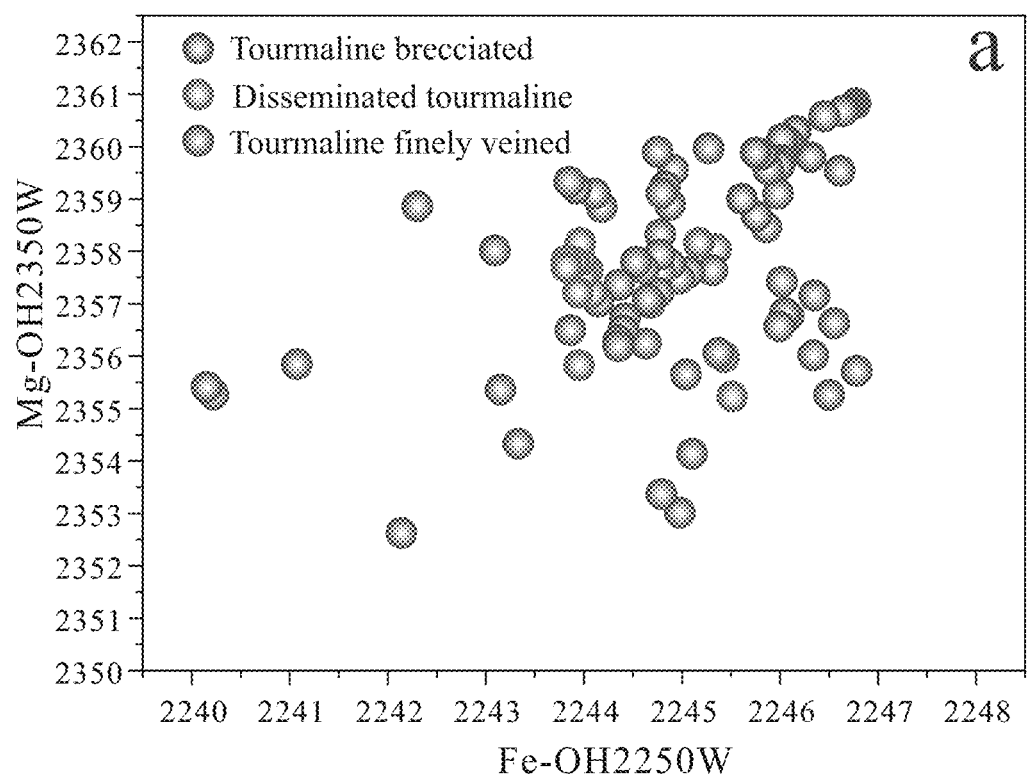
FIG. 2: a diagram showing different types and wavelength distribution of hydrothermal tourmaline in the Beimulang porphyry copper deposit.
Figure 3:
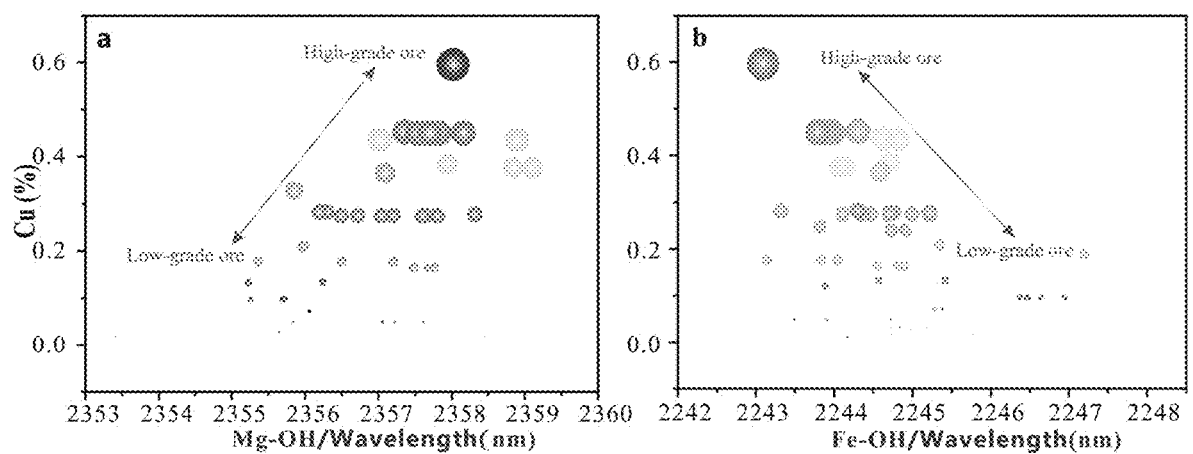
FIG. 3: a distribution diagram of relationships between Mg—OH and Fe—OH short-wave infrared wavelengths of tourmaline and copper grades in the Beimulang porphyry copper deposit.

A specific embodiment provides a method for rapid prediction of the potential of porphyry copper mineralization based on spectral characteristics of tourmaline, with reference to FIG. 1:

S1, geological data of the porphyry copper deposit are collected;
magma-fluid evolution, petrography and mineralogy related data of the Beimulang porphyry copper deposit is collected and collated, systematically.
S2, Classification and collection of tourmaline on the surface and in drill holes;
a cause of formation of tourmaline is divided into magmatic tourmaline or hydrothermal tourmaline according to a process of magma-fluid evolution of the Beimulang porphyry copper deposit, and phases and generations of the hydrothermal tourmaline closely related to mineralization are determined by combining petrographic and mineralogical characteristics with cut-through relationship and matrix support information; and hydrothermal tourmaline samples of the same phase and generation are collected, structural types include a disseminated type, a finely veined type, and tourmaline brecciated, and a collection area includes the surface, and interior and periphery of an ore body in drill holes.
S3. Sample preparation;
the obtained tourmaline samples for the short-wave infrared spectrum are washed with clean water, the surfaces of the samples are wiped clean, and the samples are dried to eliminate the influence of attached ore mineral or gangue mineral debris, and natural water on the spectral characteristics.
S4, Short-wave infrared spectroscopy measurement and testing of copper grade;
short-wave infrared spectroscopy measurement is performed on tourmaline (disseminated, finely veined, and tourmaline brecciated) samples with different structural types and the same hydrothermal origin, and spectral characteristic curves of different structural types of tourmaline are collected as much as possible to improve the representativeness of the spectral characteristics of the tourmaline.
S5, Extraction of spectral characteristic parameters of tourmaline, and data processing;
spectral characteristics of the Fe—OH wavelength and Mg—OH wavelength of the tourmaline samples in 2100-2500 nm are extracted based on The Spectral Geologist (TSG), as shown in FIG. 2. The results show that Beimulang tourmalines have Fe—OH wavelength ranges of 2240-2247 nm, and Mg—OH wavelength ranges of 2252-2261 nm, and different types of tourmaline do not show significant differences in their spectral parameters, so that finely veined, disseminated and brecciated tourmalines are from the same hydrothermal source, and formed in the same phase, and the changes in their spectral parameters can be used to discriminate the metallogenic potential. Data of locations, types, copper grades, Fe—OH wavelengths, and Mg—OH wavelengths of the tourmaline samples are collated.
S6, Evaluation of the metallogenic potential by spectral characteristics of tourmaline;
projection is performed with Fe—OH wavelength of the samples as an abscissa, and copper grades as an ordinate; and projection is performed with Mg—OH wavelength of the samples as an abscissa, and copper grades on an ordinate, as shown in FIG. 3. It is not difficult to find a law that: Fe—OH in wavelength ranges of 2240-2250 nm indicates a great potential of the porphyry copper mineralization in a short wave direction, and a small potential of the porphyry copper mineralization in a long wave direction; whereas Mg—OH in wavelength ranges of 2350-2360 nm indicates a great metallogenic potential in a long wave direction, and a small metallogenic potential in a short wave direction.

Based on this, an evaluation rule for the potential of the porphyry copper mineralization is obtained:
if the Fe—OH wavelength is less than 2245.75 nm, and the Mg—OH wavelength is greater than 2356.57 nm in the short-wave infrared spectrum of the samples, it is indicated that the porphyry copper deposit in an area where the samples are located has a great metallogenic potential; and
if the Fe—OH wavelength is greater than 2245.75 nm, and the Mg—OH wavelength is less than 2356.57 nm in the short-wave infrared spectrum of the samples, it is indicated that the porphyry copper deposit in an area where the samples are located has a small metallogenic potential.

Figure 4:
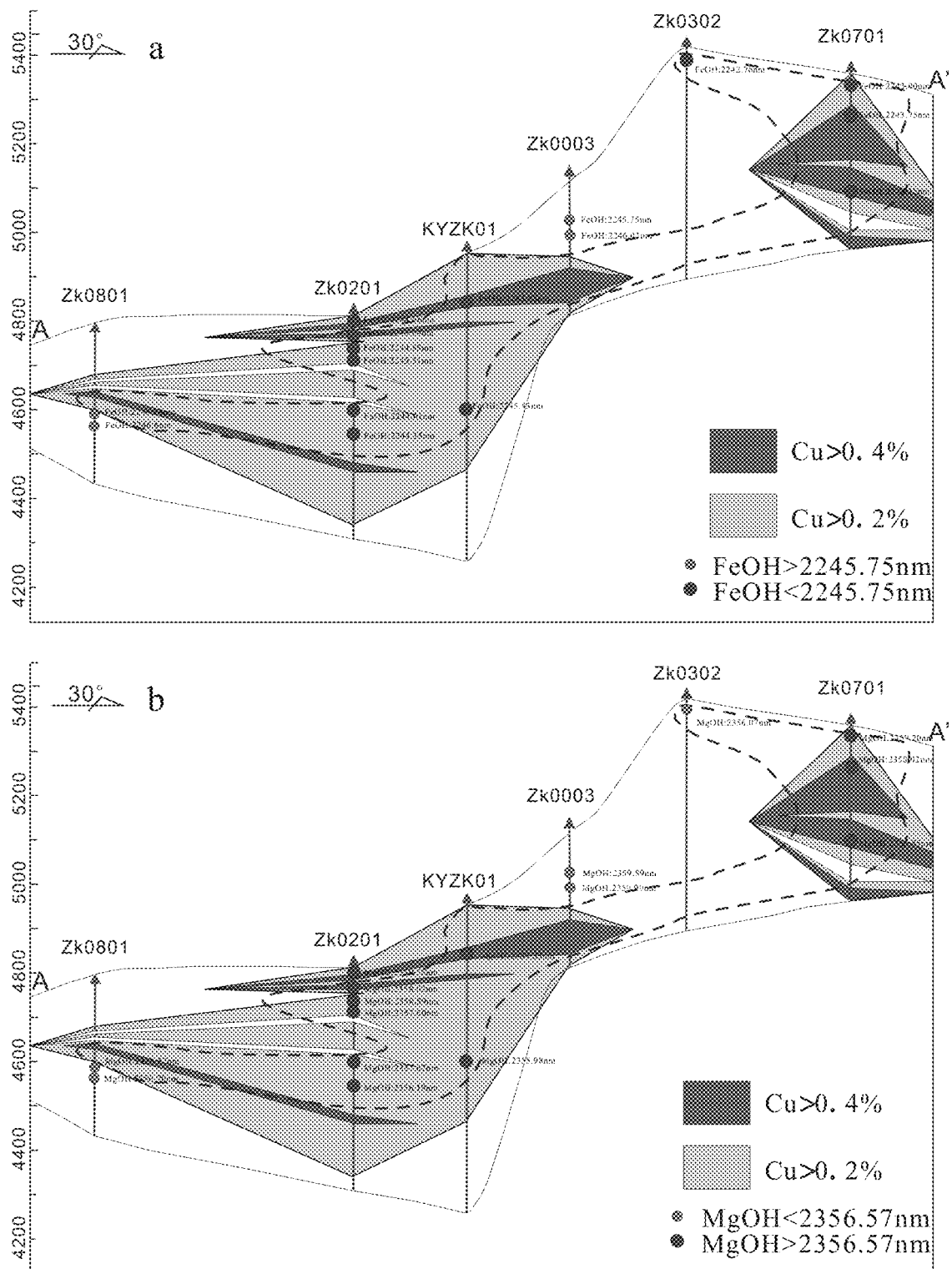
FIG. 4: a distribution diagram of relationships between Mg—OH and Fe—OH short-wave infrared wavelengths of tourmaline and copper grades in the profile of Beimulang porphyry copper deposit.

The metallogenic potential of tourmaline samples developed from 6 drill holes in a Beimulang exploration line section is evaluated based on the infrared spectral exploration identification and the evaluation rule of tourmaline minerals, and the results showed that the potential of porphyry copper mineralization in ZK0701, ZK0201 and KYZK01 is greater, and the potential of porphyry copper mineralization in ZK0003 and ZK0801 is smaller, as shown in FIG. 4. After the subsequent laboratory analysis and verification, locations with great potential of porphyry copper mineralization predicted by the spectrum of the tourmaline are basically consistent with orebody locations delineated by laboratory analysis results, which proves the effectiveness of this method, and can greatly improve the efficiency of prospecting and exploration work and shorten the exploration period.

What is claimed is:

1. A method for rapid prediction of porphyry copper mineralization potential based on spectral characteristics of tourmaline, comprising:
    (1) collecting and collating data related to magma-fluid evolution, petrography and mineralogy of a porphyry copper deposit in a working area, systematically, distinguishing magmatic tourmaline from hydrothermal tourmaline in the working area, and further distinguishing phases and generations of the hydrothermal tourmaline;
    (2) collecting hydrothermal tourmaline samples of a same phase and generation;
    (3) performing short-wave infrared spectroscopy measurement on the collected hydrothermal tourmaline samples;
    (4) extracting spectral characteristics of a Fe—OH wavelength and a Mg—OH wavelength of the hydrothermal tourmaline samples based on The Spectral Geologist (TSG); and
    (5) when the Fe—OH wavelength is less than 2245.75 nm, and the Mg—OH wavelength is greater than 2356.57 nm in the short-wave infrared spectrum of the samples, indicating that the porphyry copper deposit in an area where the samples are located has a great metallogenic potential; and when the Fe—OH wavelength is greater than 2245.75 nm, and the Mg—OH wavelength is less than 2356.57 nm in the short-wave infrared spectrum of the samples, indicating that the porphyry copper deposit in an area where the samples are located has a small metallogenic potential.

2. The method according to claim 1, wherein in the step 1, the tourmaline is divided into magmatic tourmaline or hydrothermal tourmaline according to a process of magma-fluid evolution of the porphyry copper deposit.

3. The method according to claim 1, wherein in the step 1, the phases and generations of the hydrothermal tourmaline closely related to mineralization are determined by combining petrographic and mineralogical characteristics with cut-through relationship and matrix support information.

4. The method according to claim 1, wherein a collection area in the step 2 comprises a surface, and interior and periphery of an ore body in drill holes.

5. The method according to claim 1, wherein structural types of the collected tourmaline samples in the step 2 comprise a disseminated type, a finely veined type, and a dotted type.

6. The method according to claim 5, wherein the step 3 further comprises washing and drying the collected hydrothermal tourmaline samples to avoid an influence of impurities on the spectral characteristics.

7. The method according to claim 1, wherein the step 3 further comprises washing and drying the collected hydrothermal tourmaline samples to avoid an influence of impurities on the spectral characteristics.

* * * * *